US012310598B2

(12) United States Patent
McElroy et al.

(10) Patent No.: US 12,310,598 B2
(45) Date of Patent: May 27, 2025

(54) JUNCTIONAL TOURNIQUET

(71) Applicant: Ohio State Innovation Foundation, Columbus, OH (US)

(72) Inventors: James Allen McElroy, Whipple, OH (US); Nadi Charlie Graham, Dayton, OH (US); Tanya Marie Nocera, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 369 days.

(21) Appl. No.: 17/795,508

(22) PCT Filed: Jan. 28, 2021

(86) PCT No.: PCT/US2021/015539
§ 371 (c)(1),
(2) Date: Jul. 26, 2022

(87) PCT Pub. No.: WO2021/155031
PCT Pub. Date: Aug. 5, 2021

(65) Prior Publication Data
US 2023/0107379 A1 Apr. 6, 2023

Related U.S. Application Data

(60) Provisional application No. 62/966,869, filed on Jan. 28, 2020.

(51) Int. Cl.
*A61B 17/132* (2006.01)
*A61B 17/00* (2006.01)
(52) U.S. Cl.
CPC ...... *A61B 17/1325* (2013.01); *A61B 2017/00477* (2013.01)

(58) Field of Classification Search
CPC ............ A61B 17/1325; A61B 17/1327; A61B 2017/00477
See application file for complete search history.

(56) References Cited

U.S. PATENT DOCUMENTS 1,281,653 A * 10/1918 Plummer ............ A61B 17/1327
606/203
2,604,098 A * 7/1952 Kranc ................ A61B 17/1327
606/203

(Continued)

FOREIGN PATENT DOCUMENTS

CN 109846525 A * 6/2019 ......... A61B 17/1325

OTHER PUBLICATIONS

International Searching Authority (ISA/US). International Search Report and Written Opinion, issued in PCT Application No. PCT/US2021/015539 on Jun. 3, 2021. 11 pages.

(Continued)

*Primary Examiner* — Tan-Uyen T Ho
*Assistant Examiner* — Cherie M Poland
(74) *Attorney, Agent, or Firm* — Meunier Carlin & Curfman LLC

(57) ABSTRACT

Various implementations include a junctional tourniquet device including a threaded rod, a pressure plate coupled to a second rod end, and at least one ratchet lock defining ratchet lock threads. The ratchet lock is biased toward an engaged position and urgable toward a disengaged position. The ratchet lock threads are configured to be engaged with the rod threads in the engaged position and to be disengaged with the rod threads in the disengaged position. The threaded rod is movable in a first axial direction and a second axial direction. The rod threads and the ratchet lock threads are shaped to prevent the threaded rod from moving in the first axial direction when in the engaged position and to urge the at least one ratchet lock from the engaged position to the (Continued)

disengaged position when the threaded rod is moved in the second axial direction.

22 Claims, 10 Drawing Sheets

(56) References Cited

U.S. PATENT DOCUMENTS

| | | |
|---|---|---|
| 7,947,061 B1 | 5/2011 | Reis |
| 2007/0239092 A1 | 10/2007 | Ross |
| 2010/0152770 A1* | 6/2010 | Spencer ............. A61B 17/1325 |
| | | 606/203 |
| 2011/0202089 A1 | 8/2011 | Sun |
| 2015/0272592 A1 | 10/2015 | Niemeyer et al. |

OTHER PUBLICATIONS

International Searching Authority (ISA/US). Invitation to Pay Additional Fees, issued in PCT Application No. PCT/US2021/015539 on Mar. 30, 2021. 2 pages.

\* cited by examiner

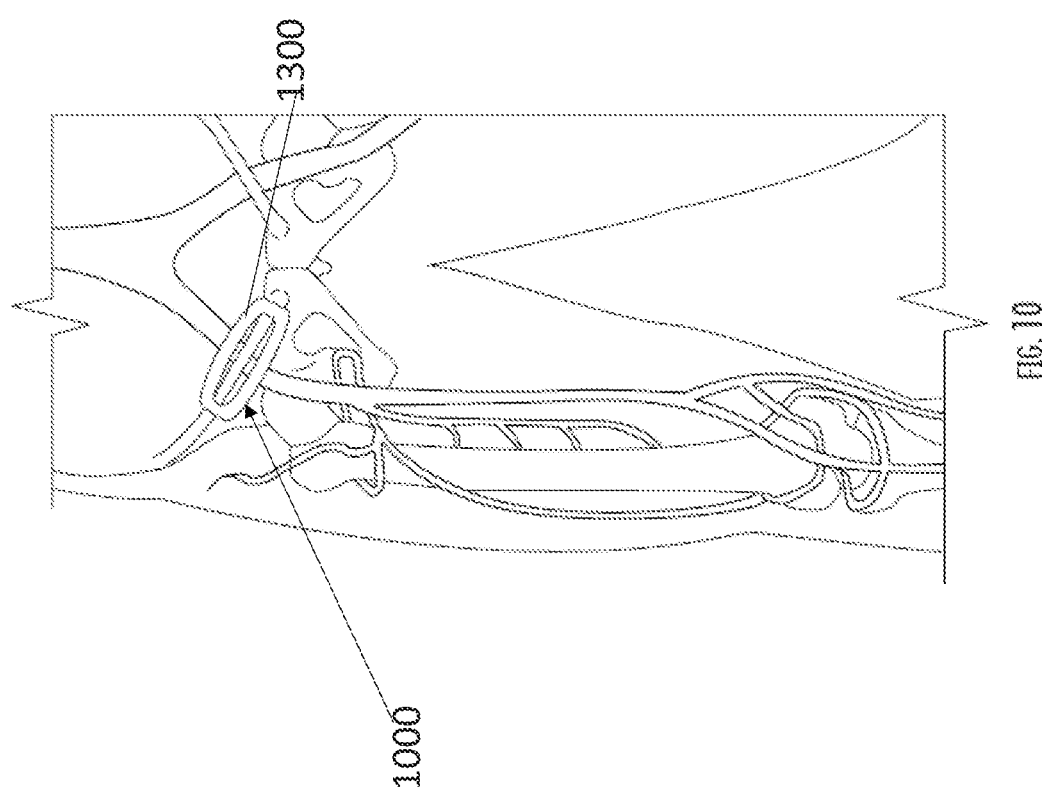

JUNCTIONAL TOURNIQUET

CROSS-REFERENCE TO RELATED APPLICATIONS

This application is a national stage application filed under 35 U.S.C. § 371 of PCT/US2021/015539 filed on Jan. 28, 2021, which claims the benefit of U.S. Provisional Patent Application No. 62/966,869, filed Jan. 28, 2020, the contents of which are incorporated herein by reference in their entirety.

BACKGROUND

Trauma is the leading cause of death in people under the age of 45. Exsanguination accounts for approximately one-third of these deaths or 1.66 MM total deaths. In combat situations, these numbers become even more staggering. A study observed all U.S. combat casualties from 2001 to 2011 (4,596). Around 90% of these combat fatalities are caused by massive blood loss. In addition, 25% of these deaths were deemed preventable had proper prehospital treatment been provided. These numbers caught the attention of the U.S. military and in 2005 regular tourniquets were given to all U.S. combat troops. Since then, combat deaths from hemorrhage have decreased by 23.5%. With preventable deaths from extremity hemorrhage greatly reduced by tourniquet use, junctional hemorrhage has surpassed extremity hemorrhage as the leading cause of death from external hemorrhage. A comprehensive study of U.S. combat fatalities from 2001 to 2011 noted that 17.5% of potentially preventable prehospital deaths resulted from junctional hemorrhage. While tourniquets designed to treat junctional wounds (junctional tourniquets) exist in the market today, they are generally inefficient and rarely used in the field.

Applying pressure to junctional areas to stop blood flow is difficult, specifically in a combat environment. This environment introduces certain constraints that would not apply to domestic/hospital situations. Junctional wounds require immediate attention as one can die from a femoral hemorrhage in 4 minutes. A normal tourniquet cannot apply pressure to the pelvic region due to the shape and size of the area. There are several other problems with existing products. These problems include the bulkiness of current solutions, slipping after application due to moving individuals, and the speed of application often being slower than alternative improvised solutions.

Thus, a need exists for a junctional tourniquet that is compact and can be quickly secured to a junctional wound.

SUMMARY

Various implementations include a junctional tourniquet device. The device includes a threaded rod. The threaded rod has a first rod end, a second rod end opposite and spaced apart from the first rod end, a rod side surface extending from the first rod end to the second rod end, and a rod longitudinal axis extending from the first rod end to the second rod end. The rod side surface defines one or more rod threads. The device includes a pressure plate coupled to the second rod end. The device also includes at least one ratchet lock defining one or more ratchet lock threads. The at least one ratchet lock is movable from an engaged position to a disengaged position. The at least one ratchet lock is biased toward the engaged position by a spring force and urgable toward the disengaged position. The one or more ratchet lock threads are configured to be engaged with the rod threads in the engaged position and to be disengaged with the rod threads in the disengaged position. The threaded rod is movable in a first axial direction and a second axial direction such that the pressure plate moves toward the at least one ratchet lock when moving in the first axial direction and the pressure plate moves away from the at least one ratchet lock when moving in the second axial direction. The rod threads, the one or more ratchet lock threads, or both are shaped to prevent the threaded rod from moving in the first axial direction when in the engaged position and to urge the at least one ratchet lock from the engaged position to the disengaged position when the threaded rod is moved in the second axial direction.

In some implementations, the device includes a spring. The spring causes the spring force.

In some implementations, the spring is a flat spring.

In some implementations, the spring includes a duct. The duct has a duct rotational axis and a radially extending duct surface defining a duct opening. The duct surface defines at least one ramp having a first ramp end and a second ramp end circumferentially spaced apart from the first ramp end. The second ramp end is radially further than the first ramp end from the duct rotational axis. A guide pin extends from the at least one ratchet lock. The guide pin is disposed within the at least one ramp. Rotation of the duct about the duct rotational axis causes the guide pin to move from the first ramp end to the second ramp end to urge the at least one ratchet lock to move from the engaged position to the disengaged position.

In some implementations, the duct includes at least one duct protrusion radially extending from the duct.

In some implementations, engagement of the one or more ratchet lock threads with the rod threads causes axial movement of the rod relative to the at least one ratchet lock when the threaded rod is rotated about the rod longitudinal axis relative to the at least one ratchet lock.

In some implementations, a knob is rotatably coupled to, and axially movable relative to, the first rod end. The knob has a knob longitudinal axis. One or more knob teeth are coupled to the knob and extend circumferentially around the knob longitudinal axis. The one or more knob teeth have a first knob tooth surface and a second knob tooth surface. One or more rod teeth are coupled to the first rod end and extend circumferentially around the rod longitudinal axis. The one or more rod teeth have a first rod tooth surface and a second rod tooth surface. The knob is rotatable in a first circumferential direction about the knob longitudinal axis. At least one first rod tooth surface positively engages a first knob tooth surface when the knob is rotated in the first circumferential direction to cause the threaded rod to rotate with the knob. The knob is rotatable in a second circumferential direction opposite the first circumferential direction about the knob longitudinal axis. At least one second rod tooth surface is slidingly engageable with a second knob tooth surface when the knob is rotated in the second circumferential direction to cause the knob to move axially away from the first rod end as the knob moves in the second circumferential direction. Axially applied force to the knob toward the first rod end causes the at least one second rod tooth surface to positively engage the second knob tooth surface when the knob is rotated in the second circumferential direction to cause the threaded rod to rotate with the knob.

In some implementations, the at least one first rod tooth surface is parallel to the rod longitudinal axis.

In some implementations, the first knob tooth surface is parallel to the knob longitudinal axis.

In some implementations, the knob has a first knob surface and a second knob surface opposite and spaced apart from the first knob surface. The one or more knob teeth are coupled to the second knob surface. At least a portion of the first knob surface is concaved.

In some implementations, the device includes a belt coupled to the duct.

In some implementations, the belt forms a closed loop with the duct.

In some implementations, the belt includes one or more belt handles.

In some implementations, the one or more belt handles include two belt handles disposed on opposite sides of the duct.

In some implementations, the belt includes a buckle.

In some implementations, the pressure plate has a first pressure plate end coupled to the second rod end and a second pressure plate end opposite and spaced apart from the first pressure plate end. The pressure plate has a tapered portion that includes the second pressure plate end. The tapered portion has a narrowest width at the second pressure plate end.

In some implementations, the first pressure plate end is pivotably coupled to the second rod end.

In some implementations, the pressure plate is omnidirectionally pivotable with respect to the post.

In some implementations, the device includes a ball joint coupling the pressure plate to the second rod end.

In some implementations, the pressure plate includes a triangular prism shape.

In some implementations, the pressure plate includes a semicylindrical shape.

In some implementations, the pressure plate includes a semispherical shape.

Various other implementations include a junctional tourniquet device. The device includes a threaded rod having a first rod end, a second rod end opposite and spaced apart from the first rod end, a rod side surface extending from the first rod end to the second rod end, and a rod longitudinal axis extending from the first rod end to the second rod end. The rod side surface defines one or more rod threads. The device includes a pressure plate coupled to the second rod end. The pressure plate has a first pressure plate end pivotably coupled to the second rod end and a second pressure plate end opposite and spaced apart from the first pressure plate end. The pressure plate has a tapered portion that includes the second pressure plate end. The tapered portion has a narrowest width at the second pressure plate end.

In some implementations, the at least one first rod tooth surface is parallel to the rod longitudinal axis.

In some implementations, the first knob tooth surface is parallel to the knob longitudinal axis.

In some implementations, the device includes a ball joint coupling the pressure plate to the second rod end.

In some implementations, the pressure plate includes a triangular prism shape.

In some implementations, the pressure plate includes a semicylindrical shape.

In some implementations, the pressure plate includes a semispherical shape.

In some implementations, the device includes a knob rotatably coupled to, and axially movable relative to, the first rod end. The knob has a knob longitudinal axis. One or more knob teeth are coupled to the knob and extend circumferentially around the knob longitudinal axis. The one or more knob teeth have a first knob tooth surface and a second knob tooth surface.

One or more rod teeth are coupled to the first rod end and extend circumferentially around the rod longitudinal axis. The one or more rod teeth have a first rod tooth surface and a second rod tooth surface. The knob is rotatable in a first circumferential direction about the knob longitudinal axis. At least one first rod tooth surface positively engages a first knob tooth surface when the knob is rotated in the first circumferential direction to cause the threaded rod to rotate with the knob. The knob is rotatable in a second circumferential direction opposite the first circumferential direction about the knob longitudinal axis. At least one second rod tooth surface is slidingly engageable with a second knob tooth surface when the knob is rotated in the second circumferential direction to cause the knob to move axially away from the first rod end as the knob moves in the second circumferential direction. Axially applied force to the knob toward the first rod end causes the at least one second rod tooth surface to positively engage the second knob tooth surface when the knob is rotated in the second circumferential direction to cause the threaded rod to rotate with the knob.

Various other implementations include a junctional tourniquet device. The device includes a threaded rod having a first rod end, a second rod end opposite and spaced apart from the first rod end, and a rod longitudinal axis. One or more rod teeth are coupled to the first rod end and extend circumferentially around the rod longitudinal axis. The one or more rod teeth have a first rod tooth surface and a second rod tooth surface. The device includes a knob rotatably coupled to, and axially movable relative to, the first rod end. The knob has a knob longitudinal axis. One or more knob teeth are coupled to the knob and extend circumferentially around the knob longitudinal axis. The one or more knob teeth have a first knob tooth surface and a second knob tooth surface. The device includes a pressure plate coupled to the second rod end. The knob is rotatable in a first circumferential direction about the knob longitudinal axis. At least one first rod tooth surface positively engages a first knob tooth surface when the knob is rotated in the first circumferential direction to cause the threaded rod to rotate with the knob. The knob is rotatable in a second circumferential direction opposite the first circumferential direction about the knob longitudinal axis. At least one second rod tooth surface is slidingly engageable with a second knob tooth surface when the knob is rotated in the second circumferential direction to cause the knob to move axially away from the first rod end as the knob moves in the second circumferential direction. Axially applied force to the knob toward the first rod end causes the at least one second rod tooth surface to positively engage the second knob tooth surface when the knob is rotated in the second circumferential direction to cause the threaded rod to rotate with the knob.

In some implementations, the at least one first rod tooth surface is parallel to the rod longitudinal axis.

In some implementations, the first knob tooth surface is parallel to the knob longitudinal axis.

BRIEF DESCRIPTION OF DRAWINGS

Example features and implementations are disclosed in the accompanying drawings. However, the present disclosure is not limited to the precise arrangements and instrumentalities shown. Similar elements in different implementations are designated using the same reference numerals.

FIG. 10 shows the pressure plate of the device of FIG. 1 engaging a femoral artery of a patient against the pelvic bone.

DETAILED DESCRIPTION

Figure 1:
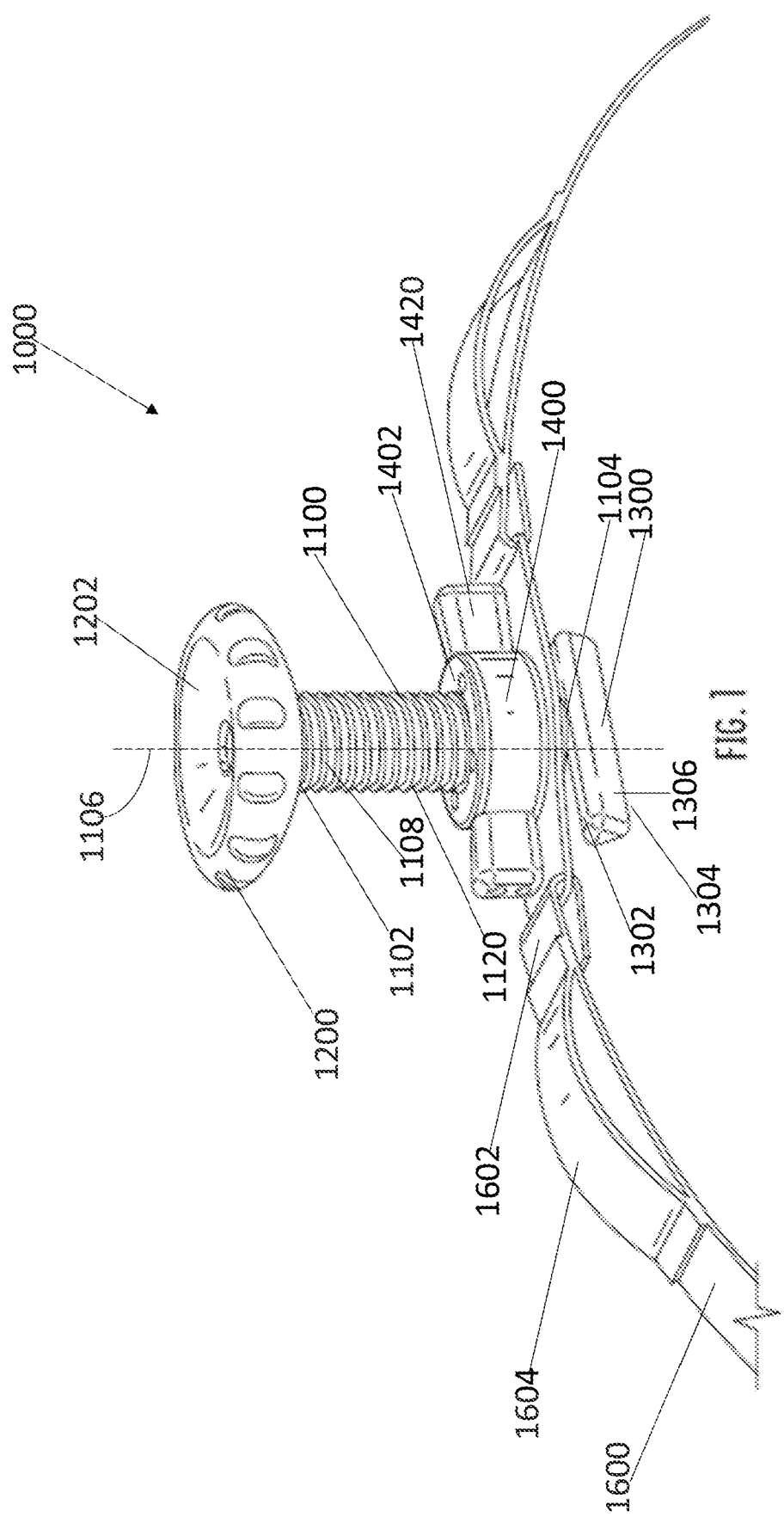
FIG. 1 is a perspective view of a junctional tourniquet device, according to one implementation.

The devices, systems, and methods disclosed herein provide for a junctional tourniquet device. The junctional tourniquet device includes a threaded rod with a knob coupled to one end and a pressure plate coupled to the opposite end. The junctional tourniquet device includes a ratcheting system to allow the threaded rod to be quickly moved in the direction of the pressure plate to apply pressure to a wound but prevents the threaded rod from moving in the opposite direction.

The knob and rod end include slanted, interlocking teeth to allow for rotation of the knob to incrementally move the threaded rod in the direction of the pressure plate. However, axial force must be applied to the knob while rotating the knob in the opposite direction to cause the threaded rod to rotate with it. The pressure plate includes a tapered portion such that a narrow portion of the pressure plate can exert a pressure on the wound.

The design of the devices, systems, and methods disclosed herein provide for junctional tourniquet devices that are compact and can be used to quickly and easily apply pressure to a wound.

For example, various implementations include a junctional tourniquet device. The device includes a threaded rod. The threaded rod has a first rod end, a second rod end opposite and spaced apart from the first rod end, a rod side surface extending from the first rod end to the second rod end, and a rod longitudinal axis extending from the first rod end to the second rod end. The rod side surface defines one or more rod threads. The device includes a pressure plate coupled to the second rod end. The device also includes at least one ratchet lock defining one or more ratchet lock threads. The at least one ratchet lock is movable from an engaged position to a disengaged position. The at least one ratchet lock is biased toward the engaged position by a spring force and urgable toward the disengaged position. The one or more ratchet lock threads are configured to be engaged with the rod threads in the engaged position and to be disengaged with the rod threads in the disengaged position. The threaded rod is movable in a first axial direction and a second axial direction such that the pressure plate moves toward the at least one ratchet lock when moving in the first axial direction and the pressure plate moves away from the at least one ratchet lock when moving in the second axial direction. The rod threads, the one or more ratchet lock threads, or both are shaped to prevent the threaded rod from moving in the first axial direction when in the engaged position and to urge the at least one ratchet lock from the engaged position to the disengaged position when the threaded rod is moved in the second axial direction.

Various other implementations also include a junctional tourniquet device in which the pressure plate has a first pressure plate end pivotably coupled to the second rod end and a second pressure plate end opposite and spaced apart from the first pressure plate end. The pressure plate has a tapered portion that includes the second pressure plate end, and the tapered portion has a narrowest width at the second pressure plate end.

Various other implementations also include a junctional tourniquet device in which one or more rod teeth are coupled to the first rod end and extending circumferentially around the rod longitudinal axis. The one or more rod teeth have a first rod tooth surface and a second rod tooth surface. The device includes a knob rotatably coupled to, and axially movable relative to, the first rod end. The knob has a knob longitudinal axis. One or more knob teeth are coupled to the knob and extend circumferentially around the knob longitudinal axis. The one or more knob teeth have a first knob tooth surface and a second knob tooth surface. The knob is rotatable in a first circumferential direction about the knob longitudinal axis. At least one first rod tooth surface positively engages a first knob tooth surface when the knob is rotated in the first circumferential direction to cause the threaded rod to rotate with the knob. The knob is rotatable in a second circumferential direction opposite the first circumferential direction about the knob longitudinal axis. At least one second rod tooth surface is slidingly engageable with a second knob tooth surface when the knob is rotated in the second circumferential direction to cause the knob to move axially away from the first rod end as the knob moves in the second circumferential direction.

FIG. 1-10 show a junctional tourniquet device 1000, according to one implementation. The junctional tourniquet device 1000 includes a threaded rod 1100, a knob 1200, a pressure plate 1300, a duct 1400 including duct protrusions 1420, two ratchet locks 1500, including two guide pins 1532, two springs 1540, and a belt 1600.

The threaded rod 1100 has a first rod end 1102 and a second rod end 1104 opposite and spaced apart from the first rod end 1102. The threaded rod 1100 has a rod side surface 1108 that extends from the first rod end 1102 to the second rod end 1104, and a rod longitudinal axis 1106 that extends from the first rod end 1102 to the second rod end 1104.

Figure 7:
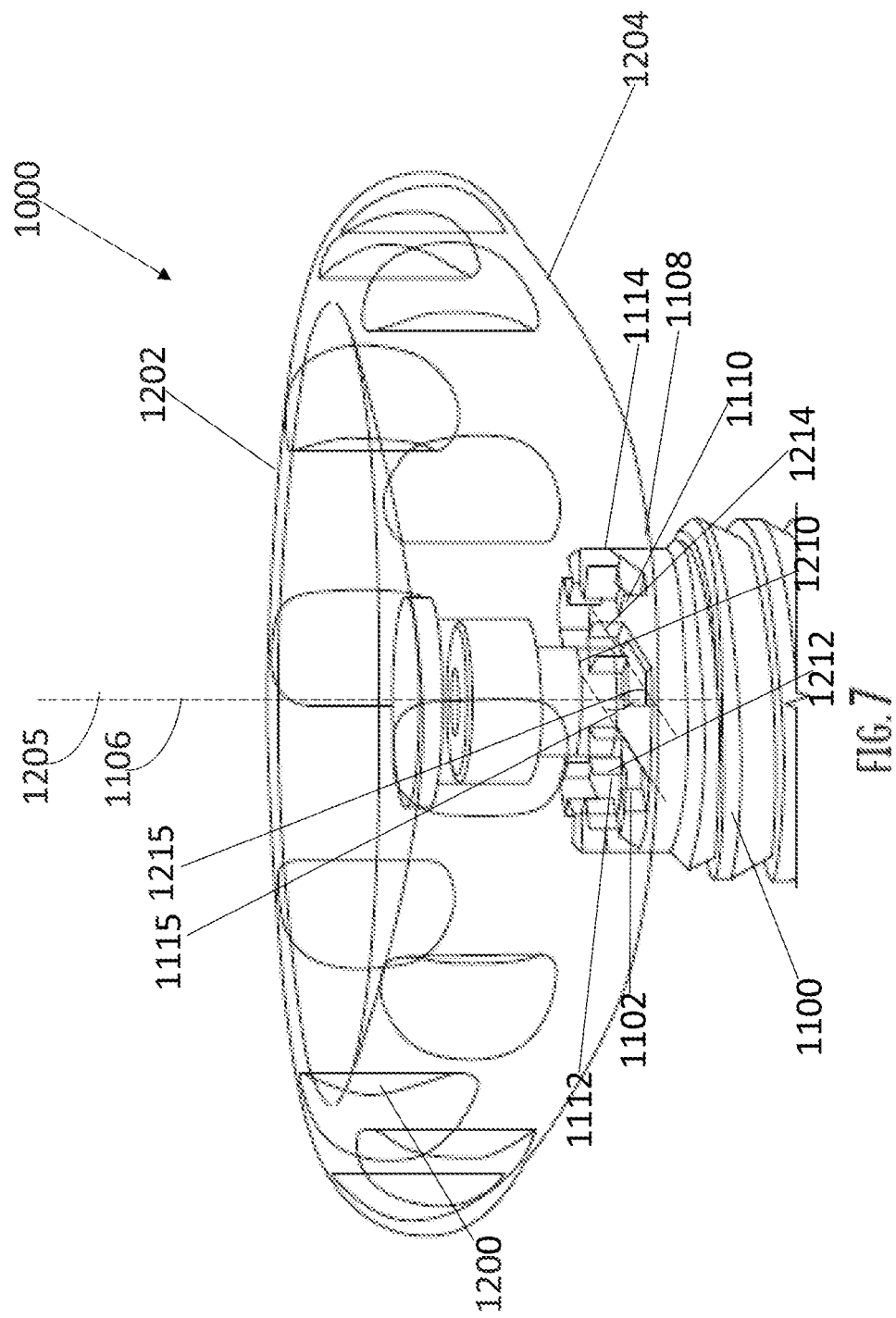
FIG. 7 is a perspective transparent view of the knob and the rod of the device of FIG. 1, showing knob teeth coupled to the knob and rod teeth coupled to the rod.
Figure 8:
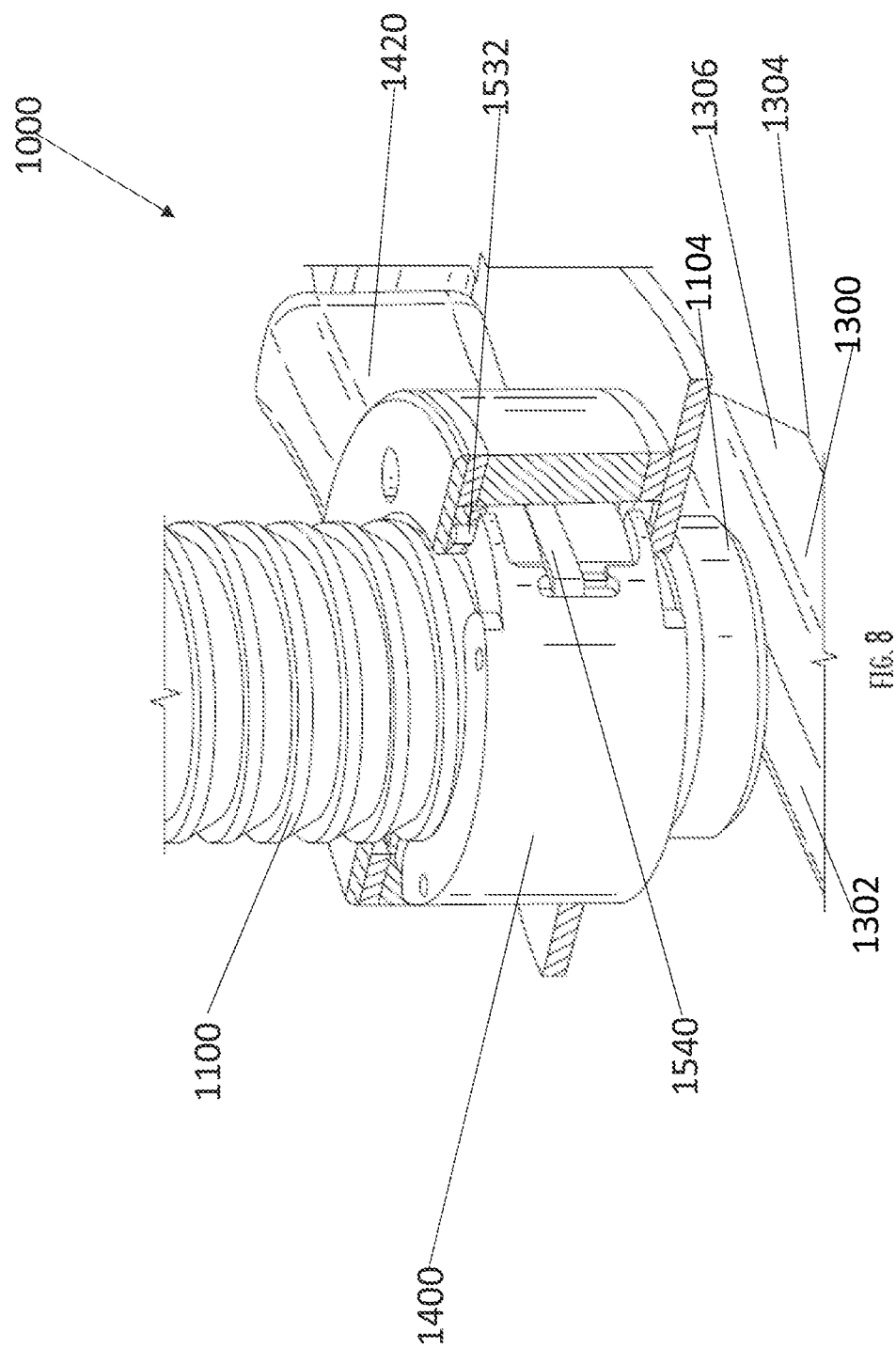
FIG. 8 is a partial cross-sectional view of the device of FIG. 1, showing the rod, the duct, one of the duct protrusions, one of the ratchet locks, one of the springs, and a portion of a pressure plate.
Figure 9:
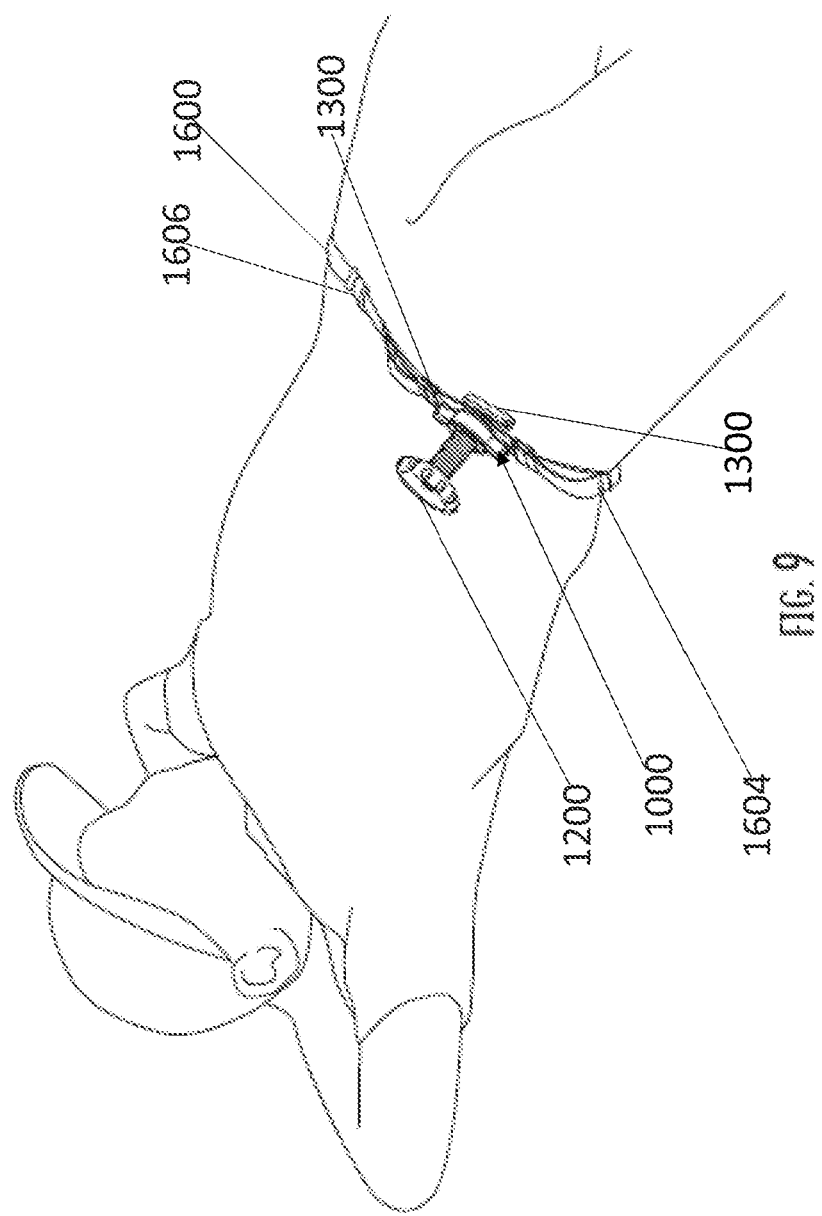
FIG. 9 shows the device of FIG. 1 secured to a patient to occlude blood flow.

As shown in FIG. 7, the first rod end 1102 includes a plurality of rod teeth 1110 that are coupled to the first rod end 1102 and extend circumferentially around the rod longitudinal axis 1106. Each of the rod teeth 1110 has a first rod tooth surface 1112 and a second rod tooth surface 1114. The first rod tooth surface 1112 is parallel to the rod longitudinal axis 1106. The second rod tooth surface 1114 is in a plane that forms a rod tooth angle 1115 with the rod longitudinal axis 1106. In the implementation shown in FIGS. 1-10, the rod tooth angle is 75 degrees.

The first rod tooth surfaces 1112 shown in FIG. 7 are parallel to the rod longitudinal axis 1106, but in some implementations, the first rod tooth surface 1112 forms any angle with the rod longitudinal axis 1106 that is 60 degrees or more and less than 180 degrees, or any other angle suitable to provide a positive engagement force with a circumferentially rotating surface. The second rod tooth surfaces 1114 form a rod tooth angle of 75 degrees with the rod longitudinal axis 1106, but in some implementations the rod tooth angle is any angle greater than 0 degrees and less than or equal to 90 degrees, or any other angle suitable to provide a slidable surface for a circumferentially rotating surface.

Figure 2:
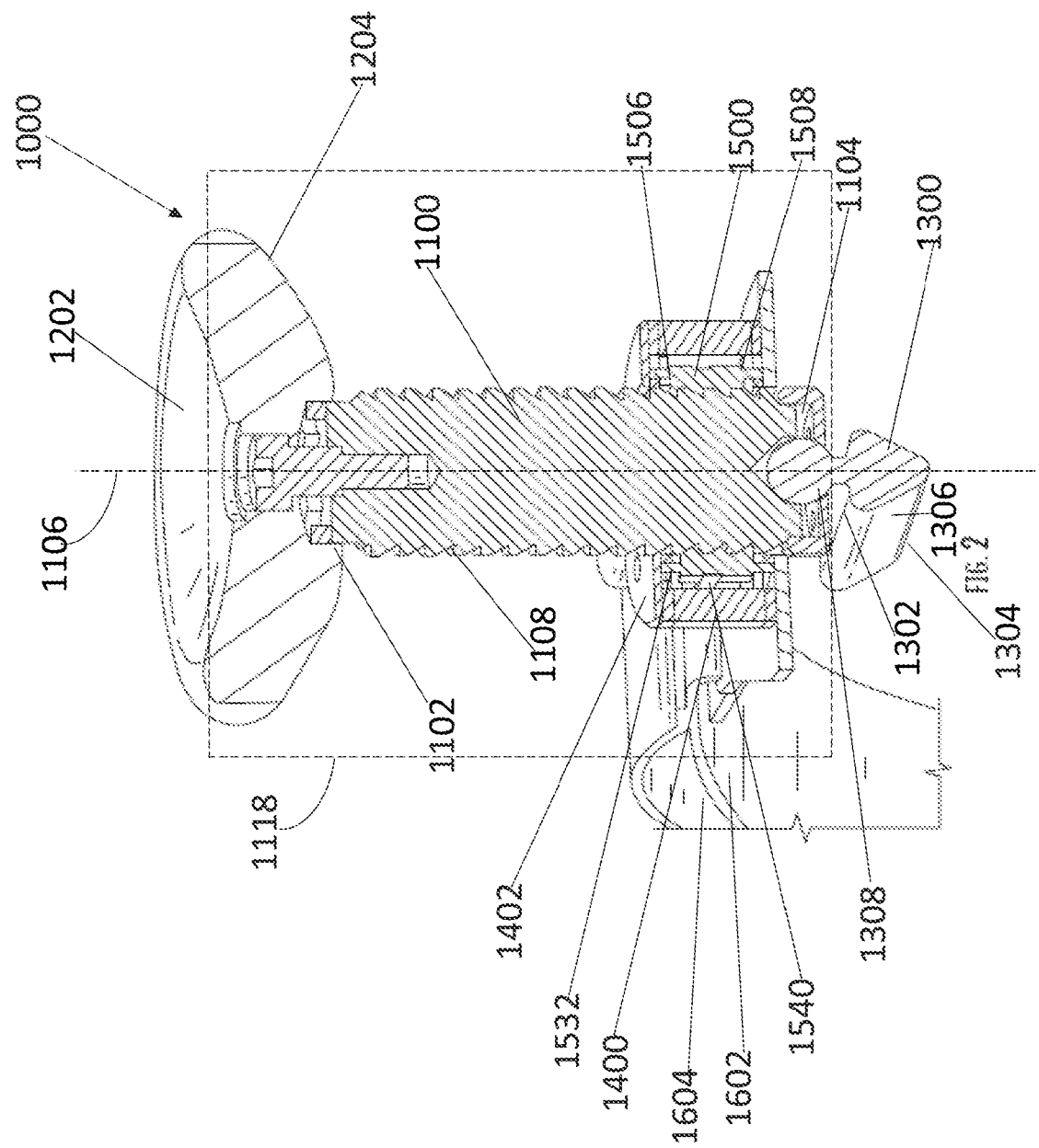
FIG. 2 is a cross-sectional view of the junctional tourniquet device of FIG. 1 along line 2-2.

As shown in FIG. 2, the second rod end includes a socket 1116 that is shaped to accept a ball joint. The socket 1116 is a depression defined by the second rod end 1104 and forms a cavity that is partially sealable to retain the ball of a ball joint within the socket 1116.

Figure 3:
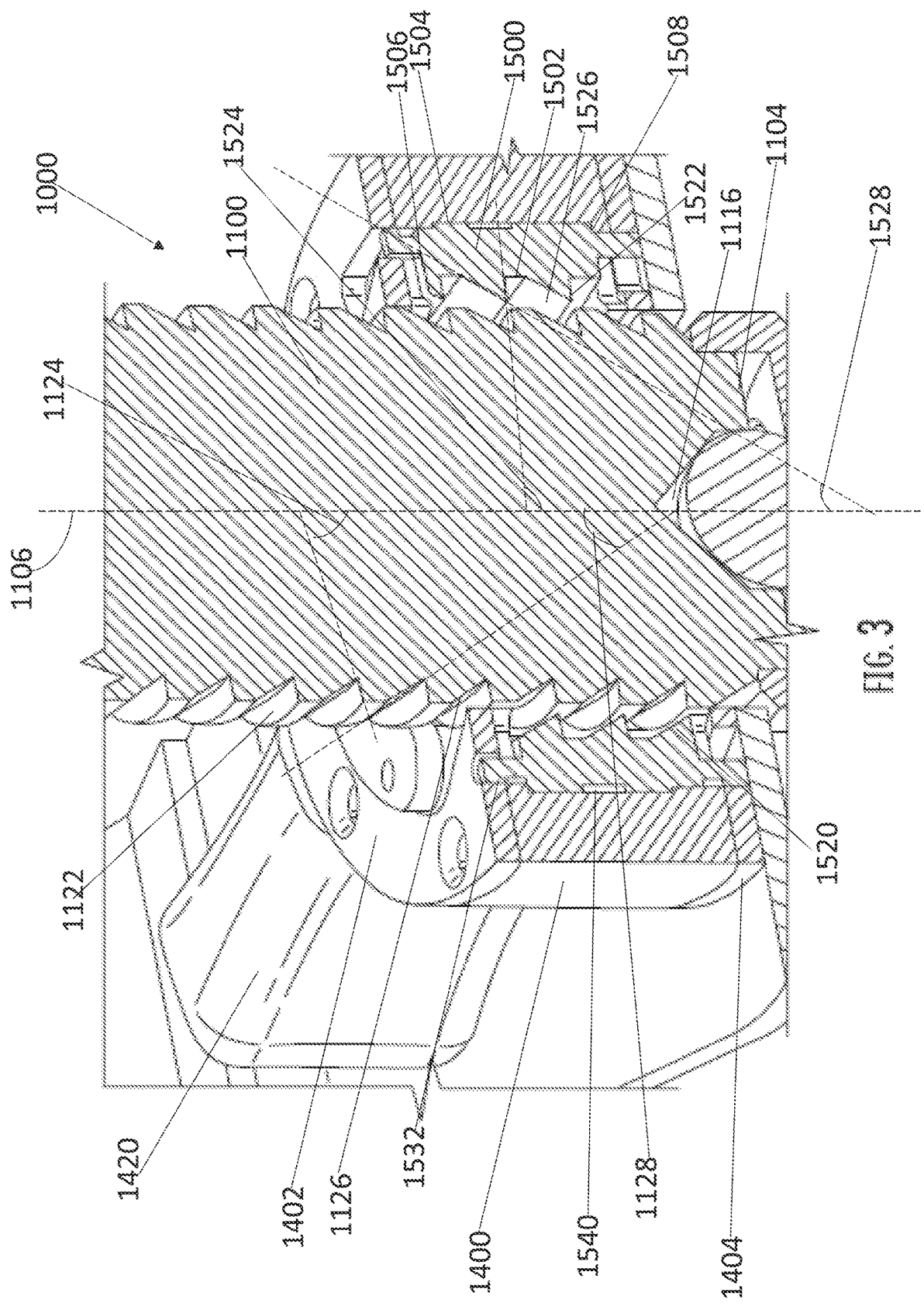
FIG. 3 is a detail perspective view of the junctional tourniquet device of FIG. 2.
Figure 4:
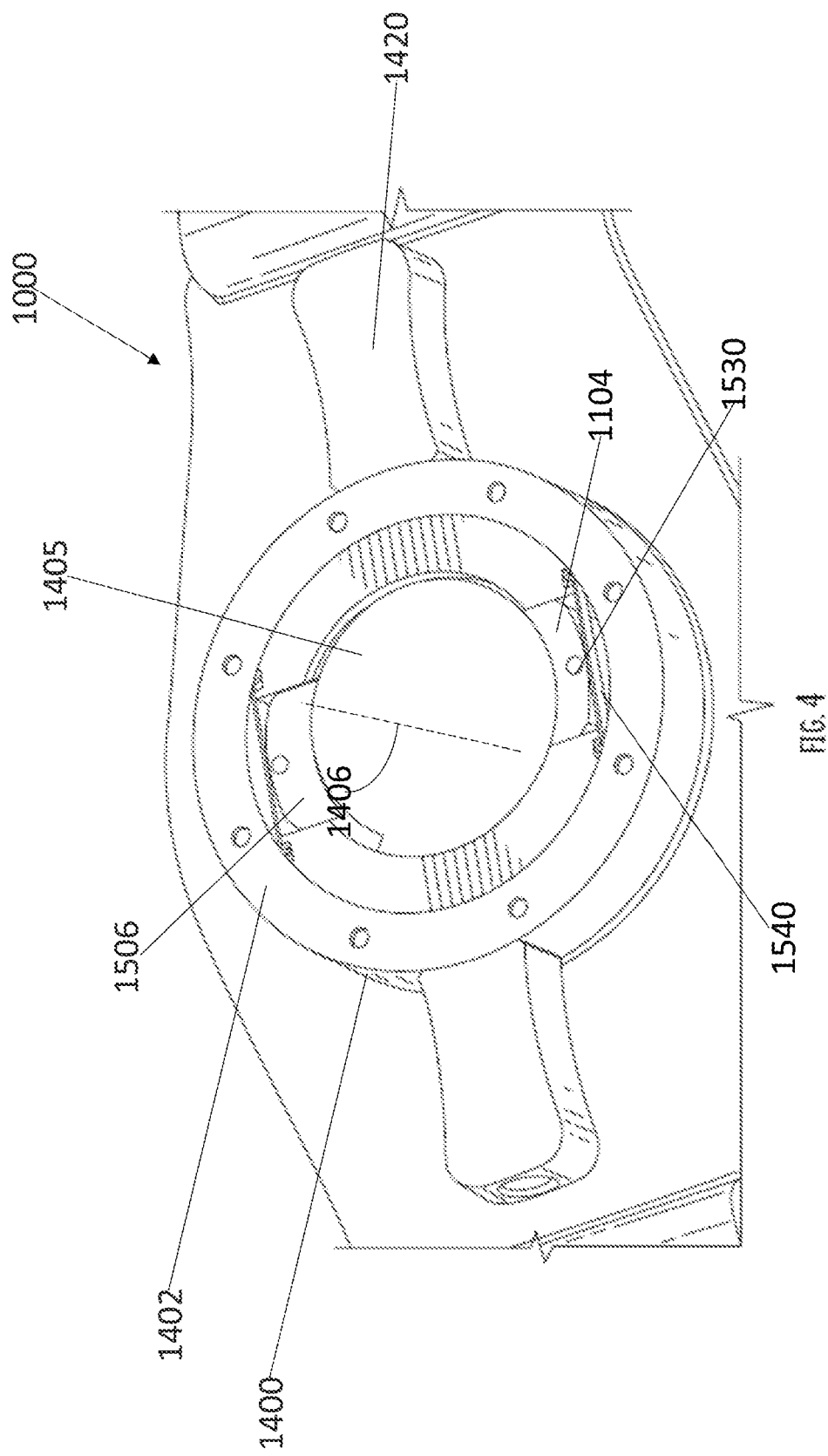
FIG. 4 is a cross-sectional view of the junctional tourniquet of FIG. 1 along line 4-4.
Figure 5:
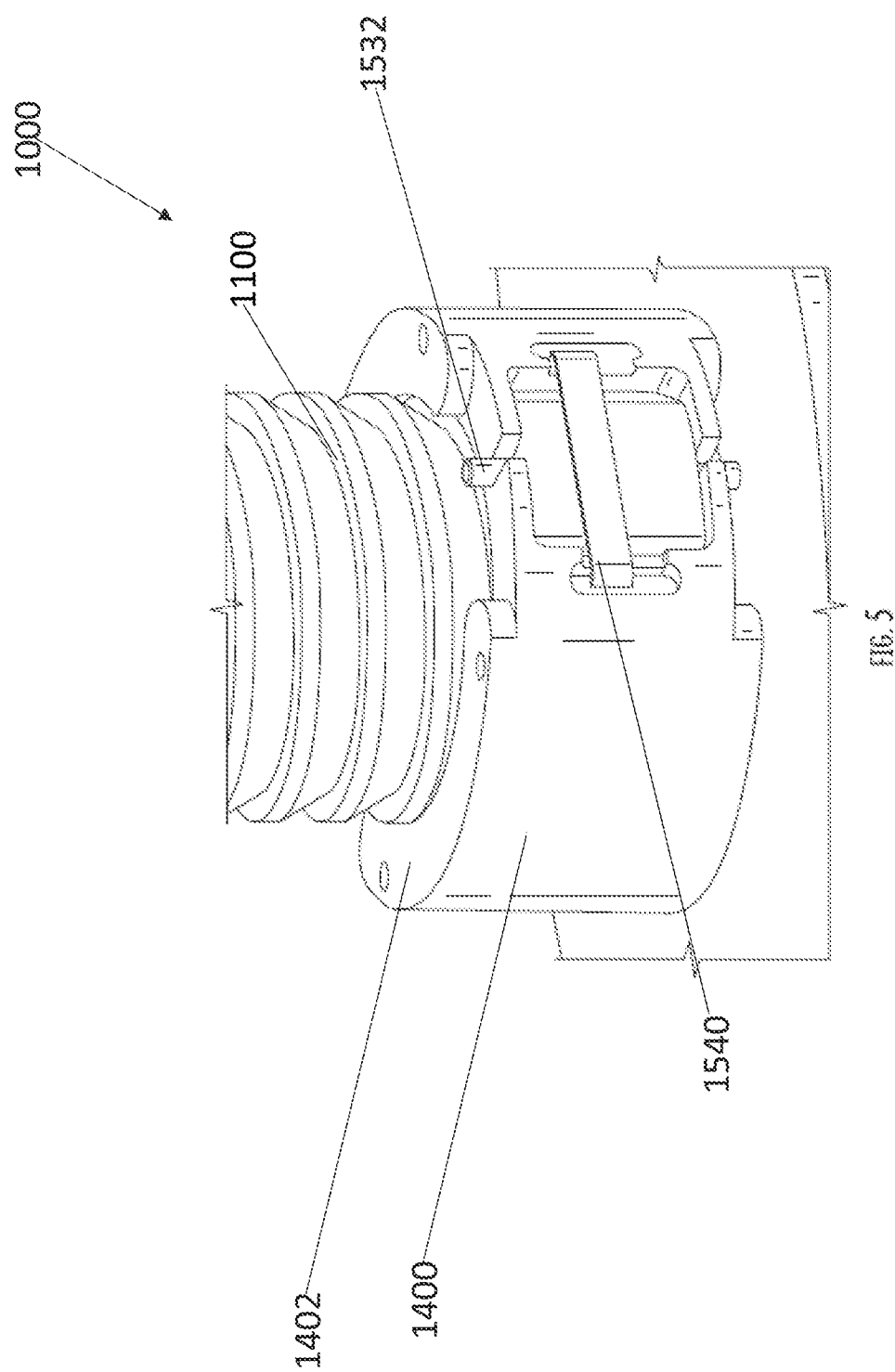
FIG. 5 is a perspective view of the device of FIG. 1 with a portion of the duct removed.
Figure 6:
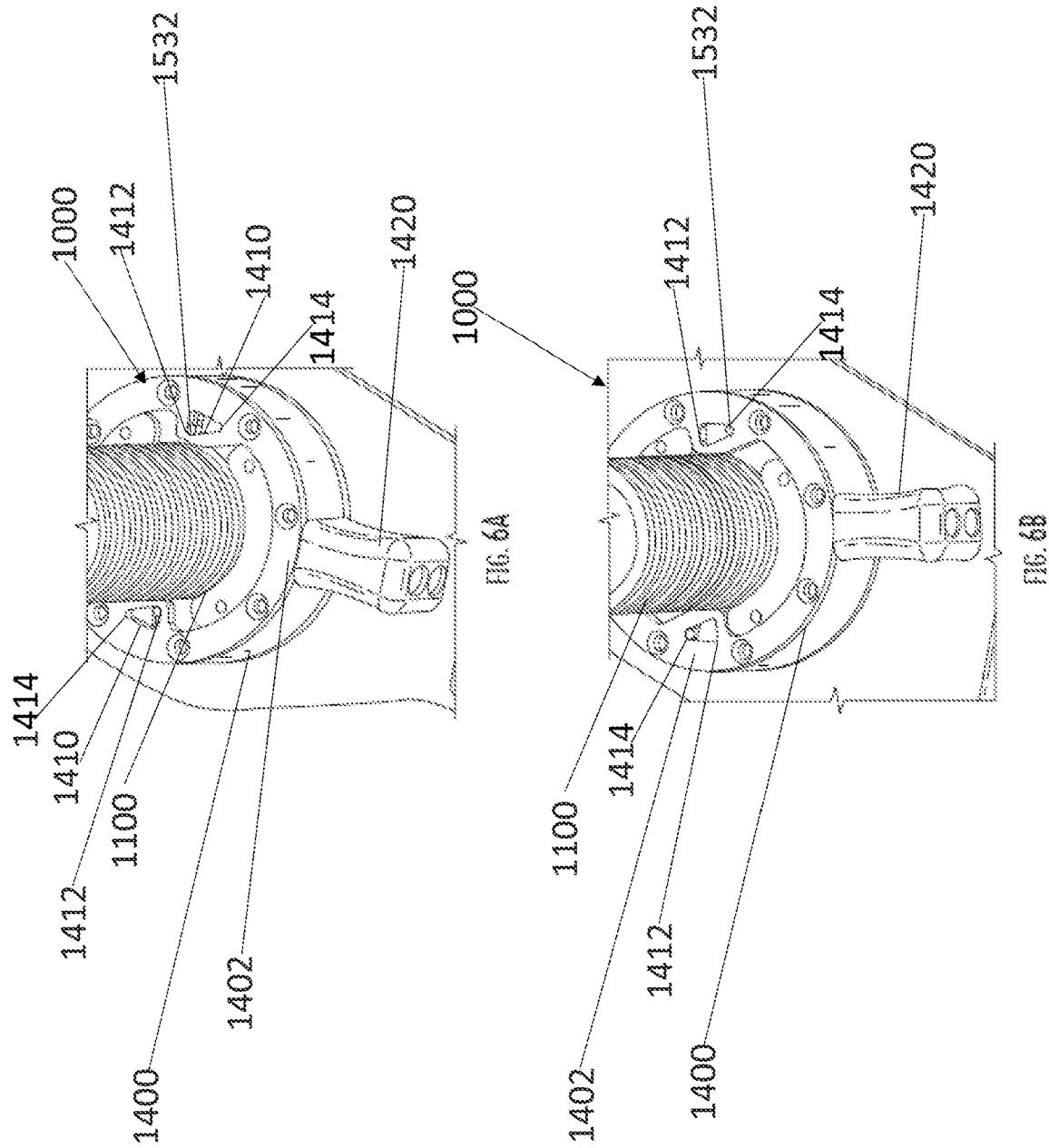
FIG. 6A is a perspective view of the device of FIG. 1, showing the position of the locking pins when in the engaged position.
FIG. 6B is a perspective view of the device of FIG. 1, showing the position of the locking pins when in the disengaged position.

The rod side surface 1108 defines a rod thread 1120 that extends helically between the first rod end 1102 and the second rod end 1104. The threaded rod 1100 includes a rod thread plane 1118 that includes the rod longitudinal axis 1106. FIGS. 2 and 3 show a cross-section of the threaded rod 1100 taken along the rod thread plane 1118. The turns of the rod thread 1120 intersect the rod thread plane 1118, and each of the rod threads 1120 have a first thread surface 1122 and a second thread surface 1124 as viewed in the rod thread plane 1118. The first thread surface 1122 of each turn is closer than the second thread surface 1124 to the first rod end 1102. The first thread surface 1122 defines a first rod thread angle 1124 with the rod longitudinal axis 1106, and the second thread surface 1124 defines a second rod thread angle 1128 with the rod longitudinal axis 1106. The second rod thread angle 1128 is less than the first rod thread angle 1124 such that each of the turns of the threads are angled toward the first rod end 1102. In the implementation shown in FIGS. 1-10, the rod side surface 1108 defines one rod thread 1120, but in some implementations, the rod side surface defines a plurality of rod threads.

The knob 1200 is a circular shaped knob 1200 that has a first knob surface 1202, a second knob surface 1204 opposite and spaced apart from the first knob surface 1202, and a knob longitudinal axis 1205. The first knob surface 1202 is concaved such that the center of the first knob surface 1202 is depressed with respect to the edges of the first knob surface 1202. As seen in FIG. 7, the second knob surface 1204 includes a plurality of knob teeth 1210 that are coupled to the second knob surface 1204 and extend circumferentially around the knob longitudinal axis 1205. Each of the knob teeth 1210 has a first knob tooth surface 1210 and a second knob tooth surface 1210. The first knob tooth surface 1210 is parallel to the knob longitudinal axis 1205. The second knob tooth surface 1210 is in a plane that forms a knob tooth angle with the knob longitudinal axis 1205. In the implementation shown in FIG. 8, the knob tooth angle is 75 degrees.

The knob 1200 is rotatably coupled to, and axially movable relative to, the first rod end 1102 such that the knob 1200 longitudinal axis is aligned with the rod longitudinal axis 1106. The knob 1200 is rotatable in a first circumferential direction about the knob longitudinal axis 1205 and in a second circumferential direction opposite the first circumferential direction about the knob longitudinal axis 1205. The first rod tooth surfaces 1112 positively engage the first knob tooth surfaces 1210 when the knob 1200 is rotated in the first circumferential direction to cause the threaded rod 1100 to rotate with the knob 1200. The second knob tooth surfaces 1210 are slidingly engageable with the second rod tooth surface 1114 when the knob is rotated in the second circumferential direction. The slidable engagement of the second knob tooth surfaces 1210 and second rod tooth surfaces 1114 slidably causes the knob 1200 to move axially away from the first rod end 1102 as the knob 1200 rotates in the second circumferential direction.

The knob 1200 shown in FIGS. 1, 2, 7, and 9 is circular shaped, but in some implementations, the knob 1200 is rectangular shaped, wedge shaped, or any other shape that is suitable for manipulating the knob 1200 to rotate about the rod longitudinal axis 1106. The knob 1200 shown in FIGS. 1, 2, 7, and 9 is concaved such that the center of the first knob 1200 surface is depressed with respect to the edges, but in some implementations the knob is flat, convex, or has a depression that is disposed off-center from the knob longitudinal axis 1205. In the implementation shown in FIGS. 1, 2, 7, and 9, the knob 1200 is rotatably coupled to the threaded rod 1100, but in some implementations, the knob is not rotatable with respect to the threaded rod. In some implementations, the knob is formed integrally with the rod.

The pressure plate 1300 is a triangular prism shape. The pressure plate 1300 has a first pressure plate end 1302, a second pressure plate end 1304 opposite and spaced apart from the first pressure plate end 1302, and a tapered portion 1306. The tapered portion 1306 includes the second pressure plate end 1304 and extends toward the first pressure plate end 1302 such that the tapered portion 1306 has a narrowest width at the second pressure plate end 1304. The pressure plate 1300 includes a ball 1308 that is coupled to the first pressure plate end 1302. The ball 1308 of the pressure plate 1300 is disposed within the socket 1116 of the second rod end 1104 to form a ball joint and pivotably couple the pressure plate 1300 to the second rod end 1104.

Although the pressure plate 1300 shown in FIGS. 1-10 is coupled to the threaded rod 1100 with a ball joint, in some implementations, the pressure plate is coupled to the threaded rod with a hinge, or any other connector that is suitable to couple the pressure plate to the threaded rod 1100. In some implementations, the pressure plate is rigidly coupled to the threaded rod, or integrally formed with the threaded rod. In the implementation shown in FIGS. 1-10 the pressure plate 1300 is omnidirectionally pivotable with respect to the threaded rod, but in some implementations the pressure plate is pivotable about one axis or two axes. Although the tapered portion 1306 shown in FIGS. 1-10 forms a triangular prism, in some implementations, the tapered portion can be any shape that varies in width, including straight, curved, or bent sides. Although the pressure plate 1300 is a triangular prism shape, in other implementations, the pressure plate is semicylindrical, semispherical, or any other shape capable of forming a contact surface against an artery or other wound.

The duct 1400 includes a duct rotational axis 1046, a radially extending first duct surface 1402, and a radially extending second duct surface 1404. The first duct surface 1402 defines a duct opening 1405 that extends from the first duct surface 1402 to the second duct surface 1404 such that the duct rotational axis 1046 extends through the center of the duct opening 1405. The threaded rod 1100 extends through the duct opening 1405, such that the duct rotational axis 1046 and the rod longitudinal axis 1106 are aligned. The threaded rod 1100 is movable relative to the duct 1400 in a first axial direction and a second axial direction in which the pressure plate 1300 moves toward the duct 1400 when moving in the first axial direction and the pressure plate 1300 moves away from the duct 1400 when moving in the second axial direction The first duct surface 1402 and the second duct surface 1404 each define two ramps 1410. Each ramp 1410 includes a first ramp end 1412 and a second ramp end 1414 circumferentially spaced apart from the first ramp end 1412. The second ramp end 1414 is radially further than the first ramp end 1412 from the duct rotational axis 1046. In the implementation shown in FIGS. 6A and 6B, the ramps 1410 form walls that define ramp slots that are formed to receive guide pins 1532, as described below.

In the implementation shown in FIGS. 1-10, the duct 1400 includes four ramps 1410, but in some implementations, the duct includes one ramp, two ramps, three ramps, or any number of ramps suitable to direct guide pins 1532.

The duct protrusions 1420 are knobs or handles that are coupled to an outer surface of the duct 1400 and include a contact surface that can be manipulated by a user to rotate the duct 1400 with respect to the duct axis. In some implementations, the duct does not include knobs and can be manipulated by directly rotating a surface of the duct.

The two ratchet locks 1500 each have an inner surface 1502, an outer surface 1504 that is opposite and spaced apart from the inner surface 1502, a first side surface 1506 that extends between the inner surface 1502 and the outer surface 1504, and a second side surface 1508 that is opposite and spaced apart from the first side surface 1506. The inner surfaces 1502 of the two ratchet locks 1500 are curved, concave surfaces extending circumferentially around the rod longitudinal axis 1106. Each of the ratchet locks 1500 are disposed radially between the duct 1400 and the threaded rod 1100 and are circumferentially spaced from each other. The ratchet locks 1500 are oriented such that the inner surface 1502 of each ratchet lock 1500 is closer than the outer surface 1504 to the rod longitudinal axis 1106.

The inner surface 1502 of each ratchet lock 1500 defines a plurality of ratchet lock threads 1520. The ratchet lock threads 1520 intersect the rod thread plane 1118, and each of the ratchet lock threads 1520 have a first lock thread surface 1522 and a second lock thread surface 1526 as viewed in the rod thread plane 1118. The first lock thread surface 1522 of each ratchet lock thread 1520 is closer than the second lock thread surface 1526 to the first side surface 1506. The first lock thread surface 1522 defines a first lock thread angle 1524 with the rod longitudinal axis 1106, and the second lock thread surface 1526 defines a second lock thread angle 1528 with the rod longitudinal axis 1106. The second lock thread angle 1528 is less than the first lock thread angle 1524. The first lock thread angle 1524 and the second lock thread angle 1528 are configured to complementarily match the first rod thread angle 1124 and the second rod thread angle 1128, respectively. In FIGS. 1-10, the first rod thread angle 1124 and first lock thread angle 1524 are 90 degrees, and the second rod thread angle 1128 and second lock thread angle 1528 are 60 degrees. In other implementations, the first rod thread angle and first lock thread angle are any angle 60 degrees or greater and less than 180 degrees or any other angle suitable to prevent movement of the threaded rod in a first axial direction when the first rod thread surface 1122 abuts the first lock thread surface 1522. In some implementations, the second rod thread angle and second lock thread angle are any angle greater than 20 degrees and less than or equal to 90 degrees or any other angle suitable to allow movement of the threaded rod in a second axial direction when the second rod thread surface 1126 abuts the second lock thread surface 1526.

The first side surface 1506 of each of the ratchet locks 1500 defines a guide pin opening 1530 extending from the first side surface 1506 to the second side surface 1508. A guide pin 1532 is disposed within each of the guide pin openings 1530 and extends from the first side surface 1506 and the second side surface 1508. Each of the guide pins 1532 is slidably disposed within one of the ramps 1410 defined by the first duct surface 1402 and within one of the ramps 1410 defined by the second duct surface 1404.

The outer surface 1504 of each of the ratchet locks 1500 defines a spring slot. A spring 1540 is disposed at least partially within each of the spring slots. In the implementation shown in FIGS. 1-10 the spring 1540 is a flat spring and the ends of the spring 1540 are slidably coupled to a portion of the duct 1400 such that the ends of the spring 1540 can slide in a circumferential direction as the spring 1540 is urged radially outwardly.

Each of the ratchet locks 1500 is movable from an engaged position to a disengaged position, in which the ratchet lock is disposed further radially inwardly in the engaged position than in the disengaged position. Each ratchet lock 1500 is biased toward the engaged position by a spring force created by the corresponding spring 1540 and urgable toward the disengaged position. The ratchet lock threads 1520 are configured to be engaged with the rod threads 1120 when the ratchet locks 1500 are in the engaged position and to be disengaged with the rod threads 1120 in the disengaged position.

Although the implementation shown in FIGS. 1-10 includes two ratchet locks 1500, in some implementations, the device 1000 includes one ratchet lock, three ratchet locks, or any number of ratchet locks suitable to secure a threaded rod in an axial direction. Although the implementation shown in FIGS. 1-10 includes three ratchet lock threads 1520, in some implementations, the ratchet lock includes one ratchet lock thread, three ratchet lock threads, or any number of ratchet lock threads suitable to engage the rod threads. Although the spring 1540 is a flat spring, in some implementations, the spring is a coil spring or any other spring suitable to urge the ratchet lock toward the rod longitudinal axis 1106. Although the guide pin 1532 is coupled to the guide pin opening 1530, in some implementations, the pin is an integrated body with the ratchet lock.

In the implementations shown in FIGS. 1-10, the device 1000 is formed from plastic. But in some implementations at least some components are formed from polymer, a metal, or any other material suitable to form a junctional tourniquet device to durably occlude bleeding from a wound.

The device 1000 also includes the belt 1600 as described above. The belt 1600 is a fabric belt that forms a closed loop with the duct 1400. The belt 1600 is removably attached to the duct 1400 using clips 1602. The belt 1600 includes two belt handles 1604 that are disposed on opposite sides of the duct 1400. The belt handles 1604 are additional pieces of fabric that form two auxiliary loops with the belt 1600. The belt 1600 also includes a buckle 1606. The buckle 1606 can be engaged and released to secure the belt 1600 around a patient at the point of an injury. Each of the buckle 1606 and the handles 1604 can be formed from plastic, metal such as aluminum, or any other material suitable to secure a tourniquet to a patient.

To operate the device 1000, a user secures the belt 1600 around a patient at a wound site such that the pressure plate 1300 second end 1304 abuts the wound. The user secures the belt handles 1604 and applies pressure to the knob 1200 in the second axial direction. As the user applies force to the knob 1200, and thus the threaded rod 1100, in the second axial direction, the second rod thread surface 1126 exerts force on the second lock thread surface 1526 to urge the ratchet locks 1500 radially outwardly to the disengaged position to allow the threaded rod 1100 to move in the second axial direction. The movement of the threaded rod 1100 in the second axial direction causes the second pressure plate end 1304 to contact the patient. As the turns of the rod thread 1120 pass the turns of the ratchet lock thread 1520, the spring 1540 causes the ratchet locks 1500 to move radially inwardly toward the engaged position, creating a ratcheting effect. The first rod thread surface 1122 and the first lock thread surface 1522 are angled to prevent the threaded rod 1100 from moving back in the first axial direction when in the engaged position.

The threaded rod 1100 can also be incrementally moved in the second axial direction by rotating the knob 1200 in the first circumferential direction. As the knob 1200 is rotated in the first circumferential direction, the first rod tooth surfaces 1112 positively engage the first lock tooth surfaces to cause the threaded rod 1100 to rotate in the first circumferential direction. The rotation of the rod threads 1120 engaged with the ratchet lock threads 1520 in the first circumferential direction causes the threaded rod 1100 to move in the second axial direction.

To incrementally move the threaded rod 1100 in the first axial direction, the user applies force to the first knob surface 1202 while rotating the knob 1200 in the second circumferential direction. As the knob 1200 is rotated in the second circumferential direction, the second rod tooth surfaces 1114 slidingly engage the second lock tooth surfaces. If enough axial force is applied to the first knob surface 1202, the second rod tooth surfaces 1114 and the second knob tooth surfaces 1212 will not slide along each other and will, instead, positively engage each other to cause the threaded rod 1100 to rotate in the second circumferential direction. The rotation of the rod threads 1120 engaged with the ratchet lock threads 1520 in the second circumferential direction causes the threaded rod 1100 to move in the first axial direction.

To release the pressure plate 1300 and allow movement of the threaded rod 1100 in the first axial direction, a user rotates the duct 1400 using the duct protrusions 1420. The guide pins 1532 engage the ramps 1410 such that the guide pins 1532 slide along the ramp 1410 from the first ramp end 1412 to the second ramp end 1414 as the duct 1400 rotates. As the guide pins 1532 move from the first ramp ends 1412 to the second ramp ends 1414, the guide pins 1532, and thus the ratchet locks 1500, are forced radially outwardly toward the disengaged position such that the threaded rod 1100 can move in the first axial direction.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A junctional tourniquet device, the device comprising:
    a threaded rod having a first rod end, a second rod end opposite and spaced apart from the first rod end, a rod side surface extending from the first rod end to the second rod end, and a rod longitudinal axis extending from the first rod end to the second rod end, the rod side surface defining one or more rod threads;
    a pressure plate coupled to the second rod end; and
    at least one ratchet lock defining one or more ratchet lock threads, wherein the at least one ratchet lock is movable from an engaged position to a disengaged position, wherein the at least one ratchet lock is biased toward the engaged position by a spring force and urgable toward the disengaged position, wherein the one or more ratchet lock threads are configured to be engaged with the rod threads in the engaged position and to be disengaged with the rod threads in the disengaged position,
    wherein the at least one ratchet lock includes
        a duct supporting the one or more ratchet lock threads, the ratchet lock threads inhibited from rotating about the rod longitudinal axis relative to the duct, and
        a duct protrusion rotatable relative to the duct to urge the ratchet lock to the disengaged position,
    wherein the threaded rod is movable in a first axial direction and a second axial direction, wherein the pressure plate moves toward the at least one ratchet lock when moving in the first axial direction and the pressure plate moves away from the at least one ratchet lock when moving in the second axial direction, and
    wherein the rod threads, the one or more ratchet lock threads, or both are shaped to prevent the threaded rod from moving in the first axial direction when in the engaged position and to urge the at least one ratchet lock from the engaged position to the disengaged position when the threaded rod is moved in the second axial direction.

2. The device of claim 1, further comprising a spring, wherein the spring causes the spring force.

3. The device of claim 2, wherein the spring comprises a flat spring.

4. The device of claim 1, wherein the duct protrusion defines a duct rotational axis and a radially extending duct surface defining a duct opening, the duct surface defining at least one ramp having a first ramp end and a second ramp end circumferentially spaced apart from the first ramp end,
    wherein the second ramp end is radially further than the first ramp end from the duct rotational axis, wherein a guide pin extends from the at least one ratchet lock, the guide pin being disposed within the at least one ramp, wherein rotation of the duct protrusion about the duct rotational axis causes the guide pin to move from the first ramp end to the second ramp end to urge the at least one ratchet lock to move from the engaged position to the disengaged position.

5. The device of claim 1, wherein a knob is rotatably coupled to, and axially movable relative to, the first rod end, the knob having a knob longitudinal axis, wherein one or more knob teeth are coupled to the knob and extend circumferentially around the knob longitudinal axis, the one or more knob teeth having a first knob tooth surface and a second knob tooth surface, wherein one or more rod teeth are coupled to the first rod end and extend circumferentially around the rod longitudinal axis, the one or more rod teeth having a first rod tooth surface and a second rod tooth surface, wherein the knob is rotatable in a first circumferential direction about the knob longitudinal axis, wherein at least one first rod tooth surface positively engages a first knob tooth surface when the knob is rotated in the first circumferential direction to cause the threaded rod to rotate with the knob, and wherein the knob is rotatable in a second circumferential direction opposite the first circumferential direction about the knob longitudinal axis, wherein at least one second rod tooth surface is slidingly engageable with a second knob tooth surface when the knob is rotated in the second circumferential direction to cause the knob to move axially away from the first rod end as the knob moves in the second circumferential direction, wherein axially applied force to the knob toward the first rod end causes the at least one second rod tooth surface to positively engage the second knob tooth surface when the knob is rotated in the second circumferential direction to cause the threaded rod to rotate with the knob.

6. The device of claim 5, wherein the at least one first rod tooth surface is parallel to the rod longitudinal axis.

7. The device of claim 5, wherein the first knob tooth surface is parallel to the knob longitudinal axis.

8. The device of claim 5, wherein the knob has a first knob surface and a second knob surface opposite and spaced apart from the first knob surface, wherein the one or more knob teeth are coupled to the second knob surface, wherein at least a portion of the first knob surface is concaved.

9. The device of claim 1, further comprising a belt coupled to the duct.

10. The device of claim 9, wherein the belt includes one or more belt handles.

11. The device of claim 10, wherein the one or more belt handles comprise two belt handles disposed on opposite sides of the duct.

12. The device of claim 9, wherein the belt includes a buckle.

13. The device of claim 9, wherein the belt forms a closed loop with the duct.

14. The device of claim 1, wherein the pressure plate has a first pressure plate end coupled to the second rod end and a second pressure plate end opposite and spaced apart from the first pressure plate end, and wherein the pressure plate has a tapered portion that includes the second pressure plate end, wherein the tapered portion has a narrowest width at the second pressure plate end.

15. The device of claim 14, wherein the first pressure plate end is pivotably coupled to the second rod end.

16. The device of claim 15, wherein the pressure plate is omnidirectionally pivotable with respect to the rod.

17. The device of claim 1, further comprising a ball joint coupling the pressure plate to the second rod end.

18. The device of claim 1, wherein the pressure plate comprises a triangular prism shape.

19. The device of claim 1, wherein the pressure plate comprises a semicylindrical shape.

20. The device of claim 1, wherein the pressure plate comprises a semispherical shape.

21. A tourniquet comprising:
an inner duct defining a rotational axis;
a strap coupled to the inner duct;
a ratchet lock coupled to the inner duct to inhibit rotation of the ratchet lock relative to the inner duct about the rotational axis and movable radially with respect to the rotational axis between an engaged position and a disengaged position;
an outer duct rotationally coupled to the inner duct and coupled to the ratchet lock so that rotation of the outer duct relative to the inner duct about the rotational axis moves the ratchet lock from the engaged position to the disengaged position; and
a threaded rod engaged with the ratchet lock in the engaged position and disengaged with the ratchet lock in the disengaged position.

22. The tourniquet of claim 21, further comprising a spring coupled to the ratchet lock and biasing the ratchet lock toward the engaged position.

* * * * *